United States Patent [19]
Rothe et al.

[11] Patent Number: 5,843,721
[45] Date of Patent: Dec. 1, 1998

[54] NUCLEIC ACIDS ENCODING HUMAN NIK PROTEIN

[75] Inventors: Mike Rothe, San Mateo; Lin Wu, South San Francisco, both of Calif.

[73] Assignee: Tularik Inc., South San Francisco, Calif.

[21] Appl. No.: 887,518

[22] Filed: Jul. 3, 1997

[51] Int. Cl.⁶ .............................. C12P 21/06; C12N 1/00; C12N 5/10; C12N 15/12
[52] U.S. Cl. ..................... 435/69.2; 435/69.1; 435/243; 435/320.1; 435/325; 435/410; 536/23.1; 536/23.5; 536/24.31
[58] Field of Search .................... 536/23.1, 23.5, 536/24.31; 435/194, 325, 410, 243, 69.1, 320.1, 69.2

[56] References Cited

PUBLICATIONS

Malinin et al, Nature, Feb. 6, 1997, vol. 385: pp. 540–544.

*Primary Examiner*—Terry A. McKelvey
*Attorney, Agent, or Firm*—Richard Aron Osman

[57] ABSTRACT

The invention provides methods and compositions relating to a novel kinase, NIK, involved in NFκB activation. The polypeptides may be produced recombinantly from transformed host cells from the disclosed NIK encoding nucleic acids or purified from human cells. The invention provides isolated NIK hybridization probes and primers capable of specifically hybridizing with the disclosed NIK genes, NIK-specific binding agents such as specific antibodies, and methods of making and using the subject compositions in diagnosis, therapy and in the biopharmaceutical industry.

15 Claims, No Drawings

5,843,721

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 3156 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
ATGGCAGTGA TGGAAATGGC CTGCCCAGGT GCCCCTGGCT CAGCAGTGGG GCAGCAGAAG      60
GAACTCCCCA AAGCCAAGGA GAAGACGCCG CCACTGGGGA AGAAACAGAG CTCCGTCTAC     120
AAGCTTGAGG CCGTGGAGAA GAGCCCTGTG TTCTGCGGAA AGTGGGAGAT CCTGAATGAC     180
GTGATTACCA AGGGCACAGC CAAGGAAGGC TCCGAGGCAG GCCAGCTGC CATCTCTATC      240
ATCGCCCAGG CTGAGTGTGA GAATAGCCAA GAGTTCAGCC CCACCTTTTC AGAACGCATT     300
TTCATCGCTG GGTCCAAACA GTACAGCCAG TCCGAGAGTC TTGATCAGAT CCCCAACAAT     360
GTGGCCCATG CTACAGAGGG CAAAATGGCC CGTGTGTGTT GGAAGGGAAA GCGTCGCAGC     420
AAAGCCCGGA AGAAACGGAA GAAGAAGAGC TCAAAGTCCC TGGCTCATGC AGGAGTGGCC     480
TTGGCCAAAC CCCTCCCCAG GACCCCTGAG CAGGAGAGCT GCACCATCCC AGTGCAGGAG     540
GATGAGTCTC CACTCGGCGC CCCATATGTT AGAAACACCC GCAGTTCAC CAAGCCTCTG      600
AAGGAACCAG GCCTTGGGCA ACTCTGTTTT AAGCAGCTTG GCGAGGGCCT ACGGCCGGCT     660
CTGCCTCGAT CAGAACTCCA CAAACTGATC AGCCCCTTGC AATGTCTGAA CCACGTGTGG     720
AAACTGCACC ACCCCAGGA CGGAGGCCCC CTGCCCCTGC CCACGCACCC CTTCCCCTAT      780
AGCAGACTGC CTCATCCCTT CCCATTCCAC CCTCTCCAGC CCTGGAAACC TCACCCTCTG     840
GAGTCCTTCC TGGGCAAACT GGCCTGTGTA GACAGCCAGA AACCCTTGCC TGACCCACAC     900
CTGAGCAAAC TGGCCTGTGT AGACAGTCCA AAGCCCCTGC CTGGCCACA CCTGGAGCCC      960
AGCTGCCTGT CTCGTGGTGC CCATGAGAAG TTTTCTGTGG AGGAATACCT AGTGCATGCT    1020
CTGCAAGGCA GCGTGAGCTC AAGCCAGGCC CACAGCCTGA CCAGCCTGGC CAAGACCTGG    1080
GCAGCACGGG GCTCCAGATC CCGGGAGCCC AGCCCCAAAA CTGAGGACAA CGAGGGTGTC    1140
CTGCTCACTG AGAAACTCAA GCCAGTGGAT TATGAGTACC GAGAAGAAGT CCACTGGGCC    1200
ACGCACCAGC TCCGCCTGGG CAGAGGCTCC TTCGGAGAGG TGCACAGGAT GGAGGACAAG    1260
CAGACTGGCT TCCAGTGCGC TGTCAAAAAG GTGCGGCTGG AAGTATTTCG GCAGAGGAG     1320
CTGATGGCAT GTGCAGGATT GACCTCACCC AGAATTGTCC CTTTGTATGG AGCTGTGAGA    1380
GAAGGGCCTT GGGTCAACAT CTTCATGGAG CTGCTGGAAG GTGGCTCCCT GGGCCAGCTG    1440
GTCAAGGAGC AGGGCTGTCT CCCAGAGGAC CGGGCCCTGT ACTACCTGGG CCAGGCCCTG    1500
GAGGGTCTGG AATACCTCCA CTCACGAAGG ATTCTGCATG GGACGTCAA AGCTGACAAC    1560
GTGCTCCTGT CCAGCGATGG GAGCCACGCA GCCCTCTGTG ACTTTGGCCA TGCTGTGTGT    1620
CTTCAACCTG ATGGCCTGGG AAAGTCCTTG CTCACAGGGG ACTACATCCC TGGCACAGAG    1680
ACCCACATGG CTCCGGAGGT GGTGCTGGGC AGGAGCTGCG ACGCCAAGGT GGATGTCTGG    1740
AGCAGCTGCT GTATGATGCT GCACATGCTC AACGGCTGCC ACCCCTGGAC TCAGTTCTTC    1800
```

| | | | | |
|---|---|---|---|---|
| CGAGGGCCGC | TCTGCCTCAA | GATTGCCAGC | GAGCCTCCGC | CTGTGAGGGA | GATCCCACCC | 1860 |
| TCCTGCGCCC | CTCTCACAGC | CCAGGCCATC | CAAGAGGGC | TGAGGAAAGA | GCCCATCCAC | 1920 |
| CGCGTGTCTG | CAGCGGAGCT | GGGAGGGAAG | GTGAACCGGG | CACTACAGCA | AGTGGGAGGT | 1980 |
| CTGAAGAGCC | CTTGGAGGGG | AGAATATAAA | GAACCAAGAC | ATCCACCGCC | AAATCAAGCC | 2040 |
| AATTACCACC | AGACCCTCCA | TGCCCAGCCG | AGAGAGCTTT | CGCCAAGGGC | CCCAGGGCCC | 2100 |
| CGGCCAGCTG | AGGAGACAAC | AGGCAGAGCC | CCTAAGCTCC | AGCCTCCTCT | CCCACCAGAG | 2160 |
| CCCCCAGAGC | CAAACAAGTC | TCCTCCCTTG | ACTTTGAGCA | AGGAGGAGTC | TGGGATGTGG | 2220 |
| GAACCCTTAC | CTCTGTCCTC | CCTGGAGCCA | GCCCCTGCCA | GAAACCCCAG | CTCACCAGAG | 2280 |
| CGGAAAGCAA | CCGTCCCGGA | GCAGGAACTG | CAGCAGCTGG | AAATAGAATT | ATTCCTCAAC | 2340 |
| AGCCTGTCCC | AGCCATTTTC | TCTGGAGGAG | CAGGAGCAAA | TTCTCTCGTG | CCTCAGCATC | 2400 |
| GACAGCCTCT | CCCTGTCGGA | TGACAGTGAG | AAGAACCCAT | CAAAGGCCTC | TCAAAGCTCG | 2460 |
| CGGGACACCC | TGAGCTCAGG | CGTACACTCC | TGGAGCAGCC | AGGCCGAGGC | TCGAAGCTCC | 2520 |
| AGCTGGAACA | TGGTGCTGGC | CCGGGGGCGG | CCCACCGACA | CCCCAAGCTA | TTTCAATGGT | 2580 |
| GTGAAAGTCC | AAATACAGTC | TCTTAATGGT | GAACACCTGC | ACATCCGGGA | GTTCCACCGG | 2640 |
| GTCAAAGTGG | GAGACATCGC | CACTGGCATC | AGCAGCCAGA | TCCCAGCTGC | AGCCTTCAGC | 2700 |
| TTGGTCACCA | AAGACGGGCA | GCCTGTTCGC | TACGACATGG | AGGTGCCAGA | CTCGGGCATC | 2760 |
| GACCTGCAGT | GCACACTGGC | CCCTGATGGC | AGCTTCGCCT | GGAGCTGGAG | GGTCAAGCAT | 2820 |
| GGCCAGCTGG | AGAACAGGCC | CTAACCCTGC | CCTCCACCGC | CGGCTCCACA | CTGCCGGAAA | 2880 |
| GCAGCCTTCC | TGCTCGGTGC | ACGATGCTGC | CCTGAAAACA | CAGGCTCAGC | CGTTCCCAGG | 2940 |
| GGATTGCCAG | CCCCCCGGCT | CACAGTGGGA | ACCAGGGCCT | CGCAGCAGCA | AGGTGGGGGC | 3000 |
| AAGCAGAATG | CCTCCCAGGA | TTTCACACCT | GAGCCCTGCC | CCACCCTGCT | GAAAAAACAT | 3060 |
| CCGCCACGTG | AAGAGACAGA | AGGAGGATGG | CAGGAGTTAC | CTGGGGAAAC | AAAACAGGGA | 3120 |
| TCTTTTTCTG | CCCCTGCTCC | AGTCGAGTTG | GCCTGA | | | 3156 |

( 2 ) INFORMATION FOR SEQ ID NO:2:

( i ) SEQUENCE CHARACTERISTICS:
        ( A ) LENGTH: 947 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Met Ala Val Met Glu Met Ala Cys Pro Gly Ala Pro Gly Ser Ala Val
 1               5                  10                  15

Gly Gln Gln Lys Glu Leu Pro Lys Ala Lys Glu Lys Thr Pro Pro Leu
             20                  25                  30

Gly Lys Lys Gln Ser Ser Val Tyr Lys Leu Glu Ala Val Glu Lys Ser
         35                  40                  45

Pro Val Phe Cys Gly Lys Trp Glu Ile Leu Asn Asp Val Ile Thr Lys
     50                  55                  60

Gly Thr Ala Lys Glu Gly Ser Glu Ala Gly Pro Ala Ala Ile Ser Ile
 65                  70                  75                  80

Ile Ala Gln Ala Glu Cys Glu Asn Ser Gln Glu Phe Ser Pro Thr Phe
                 85                  90                  95

Ser Glu Arg Ile Phe Ile Ala Gly Ser Lys Gln Tyr Ser Gln Ser Glu
                100                 105                 110
```

```
Ser  Leu  Asp  Gln  Ile  Pro  Asn  Asn  Val  Ala  His  Ala  Thr  Glu  Gly  Lys
          115            120                      125

Met  Ala  Arg  Val  Cys  Trp  Lys  Gly  Lys  Arg  Arg  Ser  Lys  Ala  Arg  Lys
130                      135                 140

Lys  Arg  Lys  Lys  Lys  Ser  Ser  Lys  Ser  Leu  Ala  His  Ala  Gly  Val  Ala
145                      150                 155                           160

Leu  Ala  Lys  Pro  Leu  Pro  Arg  Thr  Pro  Glu  Gln  Glu  Ser  Cys  Thr  Ile
                    165                 170                      175

Pro  Val  Gln  Glu  Asp  Glu  Ser  Pro  Leu  Gly  Ala  Pro  Tyr  Val  Arg  Asn
               180                      185                 190

Thr  Pro  Gln  Phe  Thr  Lys  Pro  Leu  Lys  Glu  Pro  Gly  Leu  Gly  Gln  Leu
          195                 200                      205

Cys  Phe  Lys  Gln  Leu  Gly  Glu  Gly  Leu  Arg  Pro  Ala  Leu  Pro  Arg  Ser
210                      215                      220

Glu  Leu  His  Lys  Leu  Ile  Ser  Pro  Leu  Gln  Cys  Leu  Asn  His  Val  Trp
225                      230                 235                           240

Lys  Leu  His  His  Pro  Gln  Asp  Gly  Gly  Pro  Leu  Pro  Leu  Pro  Thr  His
                    245                 250                      255

Pro  Phe  Pro  Tyr  Ser  Arg  Leu  Pro  His  Pro  Phe  Pro  Phe  His  Pro  Leu
               260                 265                      270

Gln  Pro  Trp  Lys  Pro  His  Pro  Leu  Glu  Ser  Phe  Leu  Gly  Lys  Leu  Ala
               275                 280                      285

Cys  Val  Asp  Ser  Gln  Lys  Pro  Leu  Pro  Asp  Pro  His  Leu  Ser  Lys  Leu
290                      295                      300

Ala  Cys  Val  Asp  Ser  Pro  Lys  Pro  Leu  Pro  Gly  Pro  His  Leu  Glu  Pro
305                 310                      315                           320

Ser  Cys  Leu  Ser  Arg  Gly  Ala  His  Glu  Lys  Phe  Ser  Val  Glu  Glu  Tyr
               325                      330                      335

Leu  Val  His  Ala  Leu  Gln  Gly  Ser  Val  Ser  Ser  Ser  Gln  Ala  His  Ser
               340                      345                      350

Leu  Thr  Ser  Leu  Ala  Lys  Thr  Trp  Ala  Ala  Arg  Gly  Ser  Arg  Ser  Arg
               355                      360                 365

Glu  Pro  Ser  Pro  Lys  Thr  Glu  Asp  Asn  Glu  Gly  Val  Leu  Leu  Thr  Glu
     370                      375                 380

Lys  Leu  Lys  Pro  Val  Asp  Tyr  Glu  Tyr  Arg  Glu  Glu  Val  His  Trp  Ala
385                      390                 395                           400

Thr  His  Gln  Leu  Arg  Leu  Gly  Arg  Gly  Ser  Phe  Gly  Glu  Val  His  Arg
                    405                 410                           415

Met  Glu  Asp  Lys  Gln  Thr  Gly  Phe  Gln  Cys  Ala  Val  Lys  Lys  Val  Arg
               420                 425                      430

Leu  Glu  Val  Phe  Arg  Ala  Glu  Glu  Leu  Met  Ala  Cys  Ala  Gly  Leu  Thr
          435                      440                      445

Ser  Pro  Arg  Ile  Val  Pro  Leu  Tyr  Gly  Ala  Val  Arg  Glu  Gly  Pro  Trp
     450                      455                 460

Val  Asn  Ile  Phe  Met  Glu  Leu  Leu  Glu  Gly  Gly  Ser  Leu  Gly  Gln  Leu
465                      470                 475                           480

Val  Lys  Glu  Gln  Gly  Cys  Leu  Pro  Glu  Asp  Arg  Ala  Leu  Tyr  Tyr  Leu
                    485                 490                      495

Gly  Gln  Ala  Leu  Glu  Gly  Leu  Glu  Tyr  Leu  His  Ser  Arg  Arg  Ile  Leu
               500                 505                      510

His  Gly  Asp  Val  Lys  Ala  Asp  Asn  Val  Leu  Leu  Ser  Ser  Asp  Gly  Ser
               515                 520                      525

His  Ala  Ala  Leu  Cys  Asp  Phe  Gly  His  Ala  Val  Cys  Leu  Gln  Pro  Asp
530                      535                      540
```

```
Gly  Leu  Gly  Lys  Ser  Leu  Leu  Thr  Gly  Asp  Tyr  Ile  Pro  Gly  Thr  Glu
545                      550                 555                      560

Thr  His  Met  Ala  Pro  Glu  Val  Val  Leu  Gly  Arg  Ser  Cys  Asp  Ala  Lys
                    565                 570                      575

Val  Asp  Val  Trp  Ser  Ser  Cys  Cys  Met  Met  Leu  His  Met  Leu  Asn  Gly
               580                 585                           590

Cys  His  Pro  Trp  Thr  Gln  Phe  Phe  Arg  Gly  Pro  Leu  Cys  Leu  Lys  Ile
          595                 600                           605

Ala  Ser  Glu  Pro  Pro  Val  Arg  Glu  Ile  Pro  Ser  Cys  Ala  Pro
610                      615                 620

Leu  Thr  Ala  Gln  Ala  Ile  Gln  Glu  Gly  Leu  Arg  Lys  Glu  Pro  Ile  His
625                      630                 635                           640

Arg  Val  Ser  Ala  Ala  Glu  Leu  Gly  Gly  Lys  Val  Asn  Arg  Ala  Leu  Gln
               645                      650                           655

Gln  Val  Gly  Gly  Leu  Lys  Ser  Pro  Trp  Arg  Gly  Glu  Tyr  Lys  Glu  Pro
               660                 665                      670

Arg  His  Pro  Pro  Pro  Asn  Gln  Ala  Asn  Tyr  His  Gln  Thr  Leu  His  Ala
          675                 680                      685

Gln  Pro  Arg  Glu  Leu  Ser  Pro  Arg  Ala  Pro  Gly  Pro  Arg  Pro  Ala  Glu
     690                      695                 700

Glu  Thr  Thr  Gly  Arg  Ala  Pro  Lys  Leu  Gln  Pro  Pro  Leu  Pro  Pro  Glu
705                      710                 715                           720

Pro  Pro  Glu  Pro  Asn  Lys  Ser  Pro  Pro  Leu  Thr  Leu  Ser  Lys  Glu  Glu
                    725                 730                           735

Ser  Gly  Met  Trp  Glu  Pro  Leu  Pro  Leu  Ser  Ser  Leu  Glu  Pro  Ala  Pro
               740                 745                      750

Ala  Arg  Asn  Pro  Ser  Ser  Pro  Glu  Arg  Lys  Ala  Thr  Val  Pro  Glu  Gln
          755                      760                 765

Glu  Leu  Gln  Gln  Leu  Glu  Ile  Glu  Leu  Phe  Leu  Asn  Ser  Leu  Ser  Gln
     770                      775                      780

Pro  Phe  Ser  Leu  Glu  Glu  Gln  Glu  Gln  Ile  Leu  Ser  Cys  Leu  Ser  Ile
785                      790                 795                           800

Asp  Ser  Leu  Ser  Leu  Ser  Asp  Asp  Ser  Glu  Lys  Asn  Pro  Ser  Lys  Ala
                    805                 810                      815

Ser  Gln  Ser  Ser  Arg  Asp  Thr  Leu  Ser  Ser  Gly  Val  His  Ser  Trp  Ser
               820                 825                 830

Ser  Gln  Ala  Glu  Ala  Arg  Ser  Ser  Trp  Asn  Met  Val  Leu  Ala  Arg
          835                      840                 845

Gly  Arg  Pro  Thr  Asp  Thr  Pro  Ser  Tyr  Phe  Asn  Gly  Val  Lys  Val  Gln
     850                      855                 860

Ile  Gln  Ser  Leu  Asn  Gly  Glu  His  Leu  His  Ile  Arg  Glu  Phe  His  Arg
865                      870                 875                           880

Val  Lys  Val  Gly  Asp  Ile  Ala  Thr  Gly  Ile  Ser  Ser  Gln  Ile  Pro  Ala
               885                 890                      895

Ala  Ala  Phe  Ser  Leu  Val  Thr  Lys  Asp  Gly  Gln  Pro  Val  Arg  Tyr  Asp
               900                 905                      910

Met  Glu  Val  Pro  Asp  Ser  Gly  Ile  Asp  Leu  Gln  Cys  Thr  Leu  Ala  Pro
          915                 920                 925

Asp  Gly  Ser  Phe  Ala  Trp  Ser  Trp  Arg  Val  Lys  His  Gly  Gln  Leu  Glu
     930                      935                 940

Asn  Arg  Pro
945
```

(2) INFORMATION FOR SEQ ID NO:3:

(i) SEQUENCE CHARACTERISTICS:
        (A) LENGTH: 745 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Met Glu Arg Pro Pro Gly Leu Arg Pro Gly Ala Gly Gly Pro Trp Glu
 1               5                  10                  15
Met Arg Glu Arg Leu Gly Thr Gly Gly Phe Gly Asn Val Cys Leu Tyr
                20                  25                  30
Gln His Arg Glu Leu Asp Leu Lys Ile Ala Ile Lys Ser Cys Arg Leu
            35                  40                  45
Glu Leu Ser Thr Lys Asn Arg Glu Arg Trp Cys His Glu Ile Gln Ile
        50                  55                  60
Met Lys Lys Leu Asn His Ala Asn Val Val Lys Ala Cys Asp Val Pro
 65                 70                  75                  80
Glu Glu Leu Asn Ile Leu Ile His Asp Val Pro Leu Leu Ala Met Glu
                85                  90                  95
Tyr Cys Ser Gly Gly Asp Leu Arg Lys Leu Leu Asn Lys Pro Glu Asn
                100                 105                 110
Cys Cys Gly Leu Lys Glu Ser Gln Ile Leu Ser Leu Leu Ser Asp Ile
            115                 120                 125
Gly Ser Gly Ile Arg Tyr Leu His Glu Asn Lys Ile Ile His Arg Asp
        130                 135                 140
Leu Lys Pro Glu Asn Ile Val Leu Gln Asp Val Gly Gly Lys Ile Ile
145                 150                 155                 160
His Lys Ile Ile Asp Leu Gly Tyr Ala Lys Asp Val Asp Gln Gly Ser
                165                 170                 175
Leu Cys Thr Ser Phe Val Gly Thr Leu Gln Tyr Leu Ala Pro Glu Leu
                180                 185                 190
Phe Glu Asn Lys Pro Tyr Thr Ala Thr Val Asp Tyr Trp Ser Phe Gly
            195                 200                 205
Thr Met Val Phe Glu Cys Ile Ala Gly Tyr Arg Pro Phe Leu His His
        210                 215                 220
Leu Gln Pro Phe Thr Trp His Glu Lys Ile Lys Lys Lys Asp Pro Lys
225                 230                 235                 240
Cys Ile Phe Ala Cys Glu Glu Met Ser Gly Glu Val Arg Phe Ser Ser
                245                 250                 255
His Leu Pro Gln Pro Asn Ser Leu Cys Ser Leu Ile Val Glu Pro Met
                260                 265                 270
Glu Asn Trp Leu Gln Leu Met Leu Asn Trp Asp Pro Gln Gln Arg Gly
            275                 280                 285
Gly Pro Val Asp Leu Thr Leu Lys Gln Pro Arg Cys Phe Val Leu Met
        290                 295                 300
Asp His Ile Leu Asn Leu Lys Ile Val His Ile Leu Asn Met Thr Ser
305                 310                 315                 320
Ala Lys Ile Ile Ser Phe Leu Leu Pro Pro Asp Glu Ser Leu His Ser
                325                 330                 335
Leu Gln Ser Arg Ile Glu Arg Glu Thr Gly Ile Asn Thr Gly Ser Gln
                340                 345                 350
Glu Leu Leu Ser Glu Thr Gly Ile Ser Leu Asp Pro Arg Lys Pro Ala
            355                 360                 365
```

| | | | | | | | | | | | | | | |
|---|---|---|---|---|---|---|---|---|---|---|---|---|---|---|
| Ser | Gln 370 | Cys | Val | Leu | Asp | Gly 375 | Val | Arg | Gly | Cys 380 | Asp | Ser | Tyr | Met | Val |
| Tyr 385 | Leu | Phe | Asp | Lys | Ser 390 | Lys | Thr | Val | Tyr | Glu 395 | Gly | Pro | Phe | Ala | Ser 400 |
| Arg | Ser | Leu | Ser | Asp 405 | Cys | Val | Asn | Tyr | Ile 410 | Val | Gln | Asp | Ser | Lys 415 | Ile |
| Gln | Leu | Pro | Ile 420 | Ile | Gln | Leu | Arg | Lys 425 | Val | Trp | Ala | Glu | Ala 430 | Val | His |
| Tyr | Val | Ser 435 | Gly | Leu | Lys | Glu | Asp 440 | Tyr | Ser | Arg | Leu | Phe 445 | Gln | Gly | Gln |
| Arg | Ala 450 | Ala | Met | Leu | Ser | Leu 455 | Leu | Arg | Tyr | Asn | Ala 460 | Asn | Leu | Thr | Lys |
| Met 465 | Lys | Asn | Thr | Leu | Ile 470 | Ser | Ala | Ser | Gln | Gln 475 | Leu | Lys | Ala | Lys | Leu 480 |
| Glu | Phe | Phe | His | Lys 485 | Ser | Ile | Gln | Leu | Asp 490 | Leu | Glu | Arg | Tyr | Ser 495 | Glu |
| Gln | Met | Thr | Tyr 500 | Gly | Ile | Ser | Ser | Glu 505 | Lys | Met | Leu | Lys | Ala 510 | Trp | Lys |
| Glu | Met | Glu 515 | Glu | Lys | Ala | Ile | His 520 | Tyr | Ala | Glu | Val | Gly 525 | Val | Ile | Gly |
| Tyr | Leu 530 | Glu | Asp | Gln | Ile | Met 535 | Ser | Leu | His | Ala | Glu 540 | Ile | Met | Glu | Leu |
| Gln 545 | Lys | Ser | Pro | Tyr | Gly 550 | Arg | Arg | Gln | Gly | Asp 555 | Leu | Met | Glu | Ser | Leu 560 |
| Glu | Gln | Arg | Ala | Ile 565 | Asp | Leu | Tyr | Lys | Gln 570 | Leu | Lys | His | Arg | Pro 575 | Ser |
| Asp | His | Ser | Tyr 580 | Ser | Asp | Ser | Thr | Glu 585 | Met | Val | Lys | Ile | Ile 590 | Val | His |
| Thr | Val | Gln 595 | Ser | Gln | Asp | Arg | Val 600 | Leu | Lys | Glu | Arg | Phe 605 | Gly | His | Leu |
| Ser | Lys 610 | Leu | Leu | Gly | Cys | Lys 615 | Gln | Lys | Ile | Ile | Asp 620 | Leu | Leu | Pro | Lys |
| Val 625 | Glu | Val | Ala | Leu | Ser 630 | Asn | Ile | Lys | Glu | Ala 635 | Asp | Asn | Thr | Val | Met 640 |
| Phe | Met | Gln | Gly | Lys 645 | Arg | Gln | Lys | Glu | Ile 650 | Trp | His | Leu | Leu | Lys 655 | Ile |
| Ala | Cys | Thr | Gln | Ser 660 | Ser | Ala | Arg | Ser | Leu 665 | Val | Gly | Ser | Ser | Leu 670 | Glu |
| Gly | Ala | Val 675 | Thr | Pro | Gln | Ala | Tyr 680 | Ala | Trp | Leu | Ala | Pro 685 | Asp | Leu | Ala |
| Glu | His 690 | Asp | His | Ser | Leu | Ser 695 | Cys | Val | Val | Thr | Pro 700 | Gln | Asp | Gly | Glu |
| Thr 705 | Ser | Ala | Gln | Met | Ile 710 | Glu | Glu | Asn | Leu | Asn 715 | Cys | Leu | Gly | His | Leu 720 |
| Ser | Thr | Ile | Ile | His 725 | Glu | Ala | Asn | Glu | Glu 730 | Gln | Gly | Asn | Ser | Met 735 | Met |
| Asn | Leu | Asp | Trp 740 | Ser | Trp | Leu | Thr | Glu 745 | | | | | | | |

( 2 ) INFORMATION FOR SEQ ID NO:4:

( i ) SEQUENCE CHARACTERISTICS:
        ( A ) LENGTH: 756 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:4:

```
Met Ser Trp Ser Pro Ser Leu Thr Thr Gln Thr Cys Gly Ala Trp Glu
 1               5                  10                  15
Met Lys Glu Arg Leu Gly Thr Gly Phe Gly Asn Val Ile Arg Trp
             20                  25                  30
His Asn Gln Glu Thr Gly Glu Gln Ile Ala Ile Lys Gln Cys Arg Gln
             35                  40                  45
Glu Leu Ser Pro Arg Asn Arg Glu Arg Trp Cys Leu Glu Ile Gln Ile
         50                  55                  60
Met Arg Arg Leu Thr His Pro Asn Val Val Ala Ala Arg Asp Val Pro
 65                  70                  75                  80
Glu Gly Met Gln Asn Leu Ala Pro Asn Asp Leu Pro Leu Leu Ala Met
                 85                  90                  95
Glu Tyr Cys Gln Gly Gly Asp Leu Arg Lys Tyr Leu Asn Gln Phe Glu
                100                 105                 110
Asn Cys Cys Gly Leu Arg Glu Gly Ala Ile Leu Thr Leu Leu Ser Asp
             115                 120                 125
Ile Ala Ser Ala Leu Arg Tyr Leu His Glu Asn Arg Ile Ile His Arg
         130                 135                 140
Asp Leu Lys Pro Glu Asn Ile Val Leu Gln Gln Gly Glu Gln Arg Leu
145                 150                 155                 160
Ile His Lys Ile Ile Asp Leu Gly Tyr Ala Lys Glu Leu Asp Gln Gly
                165                 170                 175
Ser Leu Cys Thr Ser Phe Val Gly Thr Leu Gln Tyr Leu Ala Pro Glu
             180                 185                 190
Leu Leu Glu Gln Gln Lys Tyr Thr Val Thr Val Asp Tyr Trp Ser Phe
         195                 200                 205
Gly Thr Leu Ala Phe Glu Cys Ile Thr Gly Phe Arg Pro Phe Leu Pro
     210                 215                 220
Asn Trp Gln Pro Val Gln Trp His Ser Lys Val Arg Gln Lys Ser Glu
225                 230                 235                 240
Val Asp Ile Val Val Ser Glu Asp Leu Asn Gly Thr Val Lys Phe Ser
                245                 250                 255
Ser Ser Leu Pro Tyr Pro Asn Asn Leu Asn Ser Val Leu Ala Glu Arg
             260                 265                 270
Leu Glu Lys Trp Leu Gln Leu Met Leu Met Trp His Pro Arg Gln Arg
         275                 280                 285
Gly Thr Asp Pro Thr Tyr Gly Pro Asn Gly Cys Phe Lys Ala Leu Asp
     290                 295                 300
Asp Ile Leu Asn Leu Lys Leu Val His Ile Leu Asn Met Val Thr Gly
305                 310                 315                 320
Thr Ile His Thr Tyr Pro Val Thr Glu Asp Glu Ser Leu Gln Ser Leu
                325                 330                 335
Lys Ala Arg Ile Gln Gln Asp Thr Gly Ile Pro Glu Glu Asp Gln Glu
             340                 345                 350
Leu Leu Gln Glu Ala Gly Leu Ala Leu Ile Pro Asp Lys Pro Ala Thr
         355                 360                 365
Gln Cys Ile Ser Asp Gly Lys Leu Asn Glu Gly His Thr Leu Asp Met
     370                 375                 380
Asp Leu Val Phe Leu Phe Asp Asn Ser Lys Ile Thr Tyr Glu Thr Gln
385                 390                 395                 400
```

| | | | | | | | | | | | | | | |
|---|---|---|---|---|---|---|---|---|---|---|---|---|---|---|
| Ile | Ser | Pro | Arg | Pro 405 | Gln | Pro | Glu | Ser | Val 410 | Ser | Cys | Ile | Leu | Gln 415 |
| Pro | Lys | Arg | Asn 420 | Leu | Ala | Phe | Phe | Gln 425 | Leu | Arg | Lys | Val | Trp 430 | Gly | Gln |
| Val | Trp | His 435 | Ser | Ile | Gln | Thr | Leu 440 | Lys | Glu | Asp | Cys | Asn 445 | Arg | Leu | Gln |
| Gln | Gly 450 | Gln | Arg | Ala | Ala | Met 455 | Met | Asn | Leu | Leu | Arg 460 | Asn | Asn | Ser | Cys |
| Leu 465 | Ser | Lys | Met | Lys | Asn 470 | Ser | Met | Ala | Ser | Met 475 | Ser | Gln | Gln | Leu | Lys 480 |
| Ala | Lys | Leu | Asp | Phe 485 | Phe | Lys | Thr | Ser | Ile 490 | Gln | Ile | Asp | Leu | Glu 495 | Lys |
| Tyr | Ser | Glu | Gln 500 | Thr | Glu | Phe | Gly | Ile 505 | Thr | Ser | Asp | Lys | Leu 510 | Leu | Leu |
| Ala | Trp | Arg 515 | Glu | Met | Glu | Gln | Ala 520 | Val | Glu | Leu | Cys | Gly 525 | Arg | Glu | Asn |
| Glu | Val 530 | Lys | Leu | Leu | Val | Glu 535 | Arg | Met | Met | Ala | Leu 540 | Gln | Thr | Asp | Ile |
| Val 545 | Asp | Leu | Gln | Arg | Ser 550 | Pro | Met | Gly | Arg | Lys 555 | Gln | Gly | Gly | Thr | Leu 560 |
| Asp | Asp | Leu | Glu | Glu 565 | Gln | Ala | Arg | Glu | Leu 570 | Tyr | Arg | Arg | Leu | Arg 575 | Glu |
| Lys | Pro | Arg | Asp 580 | Gln | Arg | Thr | Glu | Gly 585 | Asp | Ser | Gln | Glu | Met 590 | Val | Arg |
| Leu | Leu | Leu 595 | Gln | Ala | Ile | Gln | Ser 600 | Phe | Glu | Lys | Lys | Val 605 | Arg | Val | Ile |
| Tyr | Thr 610 | Gln | Leu | Ser | Lys | Thr 615 | Val | Val | Cys | Lys | Gln 620 | Lys | Ala | Leu | Glu |
| Leu 625 | Leu | Pro | Lys | Val | Glu 630 | Glu | Val | Val | Ser | Leu 635 | Met | Asn | Glu | Asp | Glu 640 |
| Lys | Thr | Val | Val | Arg 645 | Leu | Gln | Glu | Lys | Arg 650 | Gln | Lys | Glu | Leu | Trp 655 | Asn |
| Leu | Leu | Lys | Ile 660 | Ala | Cys | Ser | Lys | Val 665 | Arg | Gly | Pro | Val | Ser 670 | Gly | Ser |
| Pro | Asp | Ser 675 | Met | Asn | Ala | Ser | Arg 680 | Leu | Ser | Gln | Pro | Gly 685 | Gln | Leu | Met |
| Ser | Gln 690 | Pro | Ser | Thr | Ala | Ser 695 | Asn | Ser | Leu | Pro | Glu 700 | Pro | Ala | Lys | Lys |
| Ser 705 | Glu | Glu | Leu | Val | Ala 710 | Glu | Ala | His | Asn | Leu 715 | Cys | Thr | Leu | Leu | Glu 720 |
| Asn | Ala | Ile | Gln | Asp 725 | Thr | Val | Arg | Glu | Gln 730 | Asp | Gln | Ser | Phe | Thr 735 | Ala |
| Leu | Asp | Trp | Ser 740 | Trp | Leu | Gln | Thr | Glu 745 | Glu | Glu | Glu | His | Ser 750 | Cys | Leu |
| Glu | Gln | Ala 755 | Ser | | | | | | | | | | | | |

NUCLEIC ACIDS ENCODING HUMAN NIK PROTEIN

FIELD OF THE INVENTION

The field of this invention is proteins involved in transcription factor activation.

BACKGROUND

Cytokines trigger changes in gene expression by modifying the activity of otherwise latent transcription factors (Hill and Treisman, 1995). Nuclear factor κB (NF-κB) is a prominent example of how such an external stimulus is converted into an active transcription factor (Verma et al., 1995). The NF-κB system is composed of homo- and heterodimers of members of the Rel family of related transcription factors that control the expression of numerous immune and inflammatory response genes as well as important viral genes (Lenardo and Baltimore, 1989; Baeuerle and Henkel, 1994). The activity of NF-κB transcription factors is regulated by their subcellular localization (Verma et al., 1995). In most cell types, NF-κB is present as a heterodimer comprising of a 50 kDa and a 65 kDa subunit. This heterodimer is sequestered in the cytoplasm in association with IκBα a member of the IκB family of inhibitory proteins (Finco and Baldwin, 1995; Thanos and Maniatis, 1995; Verma et al., 1995). IκBα masks the nuclear localization signal of NF-κB and thereby prevents NF-κB nuclear translocation. Conversion of NF-κB into an active transcription factor that translocates into the nucleus and binds to cognate DNA sequences requires the phosphorylation and subsequent ubiquitin-dependent degradation of IκBα in the 26s proteasome. Signal-induced phosphorylation of IκBα occurs at serines 32 and 36. Mutation of one or both of these serines renders IκBα resistant to ubiquitination and proteolytic degradation (Chen et al., 1995); DiDonato, 1996 #370, Roff, 1996 #397.

The pleiotropic cytokines tumor necrosis factor (TNF) and interleukin-1 (IL-1) are among the physiological inducers of IκB phosphorylation and subsequent NF-κB activation (Osborn et al., 1989; Beg et al., 1993). Although TNF and IL-1 initiate signaling cascades leading to NF-κB activation via distinct families of cell-surface receptors (Smith et al., 1994; Dinarello, 1996), both pathways utilize members of the TNF receptor-associated factor (TRAF) family of adaptor proteins as signal transducers (Rothe et al., 1995; Hsu et al., 1996; Cao et al., 1996b). TRAF proteins were originally found to associate directly with the cytoplasmic domains of several members of the TNF receptor family including the 75 kDa TNF receptor (TNFR2), CD40, CD30, and the lymphotoxin-β receptor (Rothe et al., 1994; Hu et al., 1994; Cheng et al., 1995; Mosialos et al., 1995; Song and Donner, 1995; Sato et al., 1995; Lee et al., 1996; Gedrich et al., 1996; Ansieau et al., 1996). In addition, TRAF proteins are recruited indirectly to the 55 kDa TNF receptor (TNFR1) by the adaptor protein TRADD (Hsu et al., 1996). Activation of NF-κB by TNF requires TRAF2 (Rothe et al., 1995; Hsu et al., 1996). TRAF5 has also been implicated in NF-κB activation by members of the TNF receptor family (Nakano et al., 1996); Ishida, 1996 #240. In contrast, TRAF6 participates in NF-κB activation by IL-1 (Cao et al., 1996b). Upon IL-1 treatment, TRAF6 associates with IRAK, a serine-threonine kinase that binds to the IL-1 receptor complex (Cao et al., 1996a); Huang, 1997 #400.

An NF-κB-inducing kinase (NIK), a member of the MAP kinase kinase kinase (MAP3K) family, was identified as a TRAF2-interacting protein (Malinin et al., 1997). NIK activates NF-κB when overexpressed, and kinase-inactive mutants of NIK comprising its TRAF2-interacting C-terminal domain ($NIK_{(624-947)}$) or lacking two crucial lysine residues in its kinase domain ($NIK_{(KK429-430AA)}$) behave as dominant-negative inhibitors that suppress TNF-, IL-1-, and TRAF2-induced NF-κB activation (Malinin et al., 1997).

Here, we disclose a novel human NIK($NIK_{(Ala25)}$, which also provides the foregoing functionalities yet deviates in terms of critical sequence and structural characteristics; in particular, a Pro-Ala substitution at position 25 imposes altered protein structure. We show that the $NIK_{(Ala25)}$ variant interacts with and cross-phosphorylates the IκB Kinases α and β, IKK-α and IKK-β (see Goeddel et al. and Rothe et al., copending applications T97-006 and T97-007, respectively, filed Jul. 1, 1997). IKK-α and IKK-β have sequence similarity to the conceptual translate of a previously identified open reading frame postulated to encode a serine-threonine kinase of unknown function ('Conserved Helix-loop-helix Ubiquitous Kinase' or CHUK, Connelly and Marcu, 1995; Mock et al., 1995). Catalytically inactive mutants of the IKKs suppress NF-κB activation induced by TNF and IL-1 stimulation as well as by TRAF and NIK overexpression; transiently expressed IKKs associate with the endogenous IκBα complex; and the IKKs phosphorylate IκBα on serines 32 and 36. As used herein, Ser32 and Ser36 of IκB refers collectively to the two serine residues which are part of the consensus sequence DSGL/IXSM/L (e.g. ser 32 and 36 in IκBα, ser 19 and 23 in IκBβ, and ser 157 and 161, or 18 and 22, depending on the usage of methionines, in IκBε, respectively. In addition, we disclose that $NIK_{(Ala25)}$ associates with other members of the TRAF family, including TRAF5 and TRAF6. Catalytically inactive mutants of $NIK_{(Ala25)}$ also inhibit TRAF5- and TRAF6-induced NF-κB activation, thus providing a unifying concept for $NIK_{(Ala25)}$ as a common mediator in the NF-κB signaling cascades triggered by TNF and IL-1 downstream of TRAFs.

SUMMARY OF THE INVENTION

The invention provides methods and compositions relating to isolated NIK polypeptides, related nucleic acids, polypeptide domains thereof having NIK-specific structure and activity and modulators of NIK function, particularly IKKκ/α kinase activity. NIK polypeptides can regulate NFκB activation and hence provide important regulators of cell function. The polypeptides may be produced recombinantly from transformed host cells from the subject NIK polypeptide encoding nucleic acids or purified from mammalian cells. The invention provides isolated NIK hybridization probes and primers capable of specifically hybridizing with the disclosed NIK gene, NIK-specific binding agents such as specific antibodies, and methods of making and using the subject compositions in diagnosis (e.g. genetic hybridization screens for NIK transcripts), therapy (e.g. NIK kinase inhibitors to inhibit TNF signal transduction) and in the biopharmaceutical industry (e.g. as immunogens, reagents for isolating other transcriptional regulators, reagents for screening chemical libraries for lead pharmacological agents, etc.).

DETAILED DESCRIPTION OF THE INVENTION

The nucleotide sequence of a natural human cDNA encoding a human NIK polypeptide is shown as SEQ ID NO: 1, and the fall conceptual translate is shown as SEQ ID NO:2. This novel NIK cDNA sequence was cloned by PCR using primers designed from GenBank accesion number Y102565. The NIK polypeptides of the invention include incomplete translates of SEQ ID NO: 1 which translates and deletion mutants of SEQ ID NO:2 have human NIK-specific amino acid sequence, binding specificity or function and comprise Ala25. Preferred translates/deletion mutants comprise at least a 10 residue Ala25-containing domain of SEQ ID NO:2, preferably including residues 22–31, more preferably including residues 12–31, most preferably including residues 2–31. The subject domains provide NIK domain specific activity or function, such as NIK-specific kinase or kinase inhibitory activity, IKK-α/β (SEQ ID NO:3/4, respectively)-binding or binding inhibitory activity, TRAF1, 2, 3, 5 and/or 6 binding or binding inhibitory activity, IκB-binding or binding inhibitory activity, NFκB activating or inhibitory activity or antibody binding. Preferred domains phosphorylate at least one serine residue of IKK-α and/or β.

NIK-specific activity or finction may be determined by convenient in vitro, cell-based, or in vivo assays: e.g. in vitro binding assays, cell culture assays, in animals (e.g. gene therapy, transgenics, etc.), etc. Binding assays encompass any assay where the molecular interaction of an NIK polypeptide with a binding target is evaluated. The binding target may be a natural intracellular binding target such as an NIK substrate, a NIK regulating protein or other regulator that directly modulates NIK activity or its localization; or non-natural binding target such a specific immune protein such as an antibody, or an NIK specific agent such as those identified in screening assays such as described below. NIK-binding specificity may assayed by kinase activity or binding equilibrium constants (usually at least about $10^7 M^{-1}$, preferably at least about $10^8 M^{-1}$, more preferably at least about $10^9 M^{-1}$), by the ability of the subject polypeptide to function as negative mutants in NIK-expressing cells, to elicit NIK specific antibody in a heterologous host (e.g a rodent or rabbit), etc. In any event, the NIK binding specificity of the subject NIK polypeptides necessarily distinguishes that of the human NIK protein of Malinin et al. (1997).

The claimed NIK polypeptides are isolated or pure: an "isolated" polypeptide is unaccompanied by at least some of the material with which it is associated in its natural state, preferably constituting at least about 0.5%, and more preferably at least about 5% by weight of the total polypeptide in a given sample and a pure polypeptide constitutes at least about 90%, and preferably at least about 99% by weight of the total polypeptide in a given sample. The NIK polypeptides and polypeptide domains may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et aL, Greene Publ. Assoc., Wiley-Interscience, NY) or that are otherwise known in the art.

The invention provides binding agents specific to the claimed NIK polypeptides, including substrates, agonists, antagonists, natural intracellular binding targets, etc., methods of identifying and making such agents, and their use in diagnosis, therapy and pharmaceutical development. For example, specific binding agents are useful in a variety of diagnostic and therapeutic applications, especially where disease or disease prognosis is associated with improper utilization of a pathway involving the subject proteins, e.g. NF-κB activation. Novel NIK-specific binding agents include NIK-specific receptors, such as somatically recombined polypeptide receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as described below, etc. Agents of particular interest modulate NIK function, e.g. NIK-dependent transcriptional activation. For example, a wide variety of inhibitors of NIK IKK-α/β kinase activity may be used to regulate signal transduction involving IκB. Exemplary NIK kinase inhibitors include known classes of serine/threonine kinase (e.g. PKC) inhibitors such as competitive inhibitors of ATP and substrate binding, antibiotics, NIK-derived peptide inhibitors, esp. dominant negative deletion mutants, etc., see Tables 1 and 2. NIK specificity and activity are readily quantified in high throughput kinase assays using panels of protein kinases (see cited references and Examples).

Preferred inhibitors include natural compounds such as staurosporine (Omura S, et al. J Antibiot (Tokyo) 1995 July;48(7):535–48), produced by a marine organism, and synthetic compounds such as PD 153035, which also potently inhibits the EGF receptor protein kinase (Fry DW et al. Science 1994 Aug. 19;265(5175):1093–5). Members of the tyrphostin family of synthetic protein kinase inhibitors are also useful; these include compounds which are pure ATP competitors, compounds which are pure substrate competitors, and compounds which are mixed competitors: compete with both ATP and substrate (Levitzki A and Gazit A, Science 1995 Mar. 24;267(5205):1782–8). Additional NIK inhibitors include peptide-based substrate competitors endogenously made by the mammalian cell, e.g. PKI (protein kinase inhibitor, Seasholtz A.F. et al., Proc Natl Acad Sci USA 1995 Feb. 28;92(5):173–8 ), or proteins inhibiting cdc kinases (Correa-Bordes J and Nurse P, Cell 1995 Dec. 15;83(6):1001–9). Additional small peptide based substrate competitive kinase inhibitors and allosteric inhibitors (inhibitory mechanisms independent of ATP or substrate competition) are readily generated by established methods (Hvalby O et al. Proc Natl Acad Sci USA 1994 May 24;91(11):4761–5; Baija P, et al., Cell Immunol 1994 January153(1):28–38; Villar-Palasi C, Biochim Biophys Acta 1994 Dec. 30;1224(3):384–8; Liu W. Z., et al., Biochemistry 1994 Aug. 23;33(33):10120–6).

TABLE I

Selected Small Molecule NIK Kinase Inhibitors

| Inhibitors | Citations |
| --- | --- |
| HA-100[1] | 1. Hagiwara, M,. et al. Mol. Pharmacol. 32:7 (1987) |
| Chelerythrine[2] | 2. Herbert, J. M., et al. Biochem Biophys Res Com 172:993 (1990) |
| Staurosporin[3,4,5] | 3. Schachtele, C., et al. Biochem Biophys Res Com 151:542 (1988) |
| Calphostin C[6,7,8,9] | 4. Tamaoki, T., et al. Biochem Biophys Res Com 135:397 (1986) |
| K-252b[10] | 5. Tischler, A. S., et al. J. Neurochemistry 55:1159 (1990) |
| PCK 19–36[11] | 6. Bruns, R. F., et al. Biochem Biophys Res Com 176:288 (1991) |
| Iso-H7[12] | 7. Kobayashi, E., et al. Biochem Biophys Res Com 159:548 (1989) |
| PKC 19–31 | 8. Tamaoki, T., et al Adv 2nd Mass Phosphoprotein Res 24:497 (1990) |

TABLE I-continued

Selected Small Molecule NIK Kinase Inhibitors

| Inhibitors | Citations |
|---|---|
| H-7[13,3,14] | 9. Tamaoki, T., et al. Biotechnology 8:732 (1990) |
| H-89[15] | 10. Yasuzawa, T. J. Antibiotics 39:172 (1986) |
| KT5720[16] | 11. House, C., et al. Science 238:1726 (1987) |
| cAMP-depPKinhib[17] | 12. Quick, J., et al. Biochem. Biophys. Res. Com. 167:657 (1992) |
| A-3[18] | 13. Bouli, N. M. and Davis, M. Brain Res. 525:198 (1990) |
| HA1004[19,20] | 14. Takahashi, I., et al. J. Pharmacol. Exp. Ther. 255:1218 (1990) |
| K-252a[16,5] | 15. Chijiwa, T., et al. J. Biol. Chem. 265:5267 (1990) |
| KT5823[16] | 16. Kase, H., et al. Biochem. Biophys. Res. Com. 142:436 (1987) |
| ML-9[21] | 17. Cheng, H. C., et al. J. Biol. Chem. 261:989 (1986) |
| KT5926[22] | 18. Inagaki, M., et al. Mol. Pharmacol. 29:577 (1986) |
| | 19. Asano, T. and Hidaka, H. J Pharmaco. Exp Ther 231:141 (1984) |
| | 20. Hidaka, H., et al. Biochemistry 23:5036 (1984) |
| | 21. Nagatsu, T., et al. Biochem Biophys Res Com 143:1045 (1987) |
| | 22. Nakanishi, S., et al. Mol. Pharmacol. 37:482 (1990) |

TABLE II

Selected Peptidyl NIK Kinase Inhibitors

| | |
|---|---|
| hIKKα, residues 2–398 | NIK, residues 624–947 |
| hIKKα, residues 279–547 | NIK, residues 1–645, Ala429, Ala430 |
| hIκBβ, residues 5–381 | TRAF2, residues 225–501 |
| hIκBβ, residues 301–641 | TRAF6, residues 218–512 |

Accordingly, the invention provides methods for modulating signal transduction involving IκB in a cell comprising the step of modulating NIK kinase activity, e.g. by contacting the cell with a serine/threonine kinase inhibitor. The cell may reside in culture or in situ, i.e. within the natural host. Preferred inhibitors are orally active in mammalian hosts. For diagnostic uses, the inhibitors or other NIK binding agents are frequently labeled, such as with fluorescent, radioactive, chemiluminescent, or other easily detectable molecules, either conjugated directly to the binding agent or conjugated to a probe specific for the binding agent.

The amino acid sequences of the disclosed NIK polypeptides are used to back-translate NIK polypeptide-encoding nucleic acids optimized for selected expression systems Holler et al. (1993) Gene 136, 323–328; Martin et al. (1995) Gene 154, 150–166) or used to generate degenerate oligonucleotide primers and probes for use in the isolation of natural NIK-encoding nucleic acid sequences ("GCG" software, Genetics Computer Group, Inc, Madison Wis.). NIK-encoding nucleic acids used in NIK-expression vectors and incorporated into recombinant host cells, e.g. for expression and screening, transgenic animals, e.g. for functional studies such as the efficacy of candidate drugs for disease associated with NIK-modulated cell function, etc.

The invention also provides nucleic acid hybridization probes and replication/amplification primers having a NIK cDNA specific sequence comprising SEQ ID NO: 1, bases 72–75, and sufficient to effect specific hybridization thereto (i.e. specifically hybridize with SEQ ID NO: 1 in the presence of the NIK cDNA described by Malinin et al. (1997). Such primers or probes are at least 12, preferably at least 24, more preferably at least 36 and most preferably at least 96 bases in length. Demonstrating specific hybridization generally requires stringent conditions, for example, hybridizing in a buffer comprising 30% formamide in 5×SSPE (0.18M NaCl, 0.01M NaPO$_4$, pH7.7, 0.001M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. NIK nucleic acids can also be distinguished using alignment algorithms, such as BLASTX (Altschul et al. (1990) Basic Local Alignment Search Tool, J Mol Biol 215, 403–410).

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Recombinant nucleic acids comprising the nucleotide sequence of SEQ ID NO:1, or fragments thereof comprising SEQ ID NO:1, bases 72–75, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of NIK genes and gene transcripts and in detecting or amplifying nucleic acids encoding additional NIK homologs and structural analogs. In diagnosis, NIK hybridization probes find use in identifying wild-type and mutant NIK alleles in clinical and laboratory samples. Mutant alleles are used to generate allele-specific oligonucleotide (ASO) probes for high-throughput clinical diagnoses. In therapy, therapeutic NIK nucleic acids are used to modulate cellular expression or intracellular concentration or availability of active NIK.

The invention provides efficient methods of identifying agents, compounds or lead compounds for agents active at the level of a NIK modulatable cellular function. Generally, these screening methods involve assaying for compounds which modulate NIK interaction with a natural NIK binding target such as IKKα and/or β, TRAF1, 2, 3, 5 or 6, etc. A wide variety of assays for binding agents are provided including labeled in vitro protein-protein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

In vitro binding assays employ a mixture of components including an NIK polypeptide, which may be part of a fusion product with another peptide or polypeptide, e.g. a tag for detection or anchoring, etc. The assay mixtures comprise a natural intracellular NIK binding target. In a particular embodiment, the binding target is a a IKKα and/or β-derived substrate of NIK kinase activity. Such substrates comprise a NIK-phosphoylatable IKKα and/or β serine residue and at least 5, preferably at least 10, and more preferably at least 20 naturally occurring immediately flanking residues on each side. While native full-length binding targets may be used, it is frequently preferred to use portions (e.g. peptides) thereof so long as the portion provides binding affinity and avidity to the subject NIK polypeptide conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like ATP or ATP analogs (for kinase assays), salts, buffers, neutral proteins, e.g. albumin, detergents, protease inhibitors, nuclease inhibitors, antimicrobial agents, etc. may be used.

The resultant mixture is incubated under conditions whereby, but for the presence of the candidate pharmacological agent, the NIK polypeptide specifically binds the cellular binding target, portion or analog with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the NIK polypeptide and one or more binding targets is detected by any convenient way. For NIK kinase assays, 'binding' is generally detected by a change in the phosphorylation of a NIK substrate. In this embodiment, kinase activity may quantified by the transfer to the substrate of a labeled phosphate, where the label may provide for direct detection as radioactivity, luminescence, optical or electron density, etc. or indirect detection such as an epitope tag, etc. A variety of methods may be used to detect the label depending on the nature of the label and other assay components, e.g. through optical or electron density, radiative emissions, nonradiative energy transfers, etc. or indirectly detected with antibody conjugates, etc.

A difference in the binding affinity of the NIK polypeptide to the target in the absence of the agent as compared with the binding affinity in the presence of the agent indicates that the agent modulates the binding of the NIK polypeptide to the NIK binding target. Analogously, in the cell-based assay also described below, a difference in NIK-dependent transcriptional activation in the presence and absence of an agent indicates the agent modulates NIK function. A difference, as used herein, is statistically significant and preferably represents at least a 50%, more preferably at least a 90% difference.

PARENTHETICAL REFERENCES

Ansieau, S., et al. (1996). Proc. Natl. Acad. Sci. USA 93, 14053–14058.

Baeuerle, P. A., and Henkel, T. (1994). Annu. Rev. Immunol. 12, 141–179.

Beg, A. A., et al. (1993). Mol. Cell. Biol. 13, 3301–3310.

Cao, Z., Henzel, W. J., and Gao, X. (1996a). Science 271, 1128–1131.

Cao, Z., et al. (1996b). Nature 383, 443–446.

Chen, Z., et al.. (1995). Genes Dev. 9, 1586–1597.

Cheng, G., et al. (1995). Science 267, 1494–1498.

Connelly, M. A., and Marcu, K. B. (1995). Cell. Mol. Biol. Res. 41, 537–549.

Dinarello, C. A. (1996) Blood 87, 2095–2147.

Fields, S., and Song, O.-k. (1989). Nature 340, 245–246.

Finco, T. S., and Baldwin, A. S. (1995). Immunity 3, 263–272.

Gedrich, R. W., et al. (1996). J. Biol. Chem. 271, 12852–12858.

Hill, C. S., and Treisman, R. (1995). Cell 80, 199–211.

Hsu, H., Shu, H.-B., Pan, M.-P., and Goeddel, D. V. (1996). Cell 84, 299–308.

Hu, H. M., et al. (1994). J. Biol. Chem. 269, 30069–30072.

Lee, S. Y., et al. (1996). Proc. Natl. Acad. Sci. USA 93, 9699–9703.

Lenardo, M., and Baltimore, D. (1989). Cell 58, 227–229.

Malinin, N. L., et al. (1997). Nature 385, 540–544.

Mock et al. (1995). Genomics 27, 348–351.

Mosialos, G., et al. (1995). Cell 80, 389–399.

Nakano, H., et al. (1996). J. Biol. Chem. 271, 14661–14664.

Osborn, L., Kunkel, S., and Nabel, G. J. (1989) Proc Natl Aca Sci USA 86,2336–2340.

Rothe, M., Sarma, V., Dixit, V. M., and Goeddel, D. V. (1995) Science 269, 1424–1427.

Rothe, M., Wong, S. C., Henzel, W. J., and Goeddel, D. V. (1994). Cell 78, 681–692.

Sato, T., Irie, S., and Reed, J. C. (1995). FEBS Lett. 358, 113–118.

Schindler, U., and Baichwal, V. R. (1994). Mol. Cell. Biol. 14, 5820–5831.

Smith, C. A., Farrah, T., and Goodwin, R. G. (1994). Cell 76, 959–962.

Song, H. Y., and Donner, D. B. (1995). Biochem. J. 809, 825–829.

Thanos, D., and Maniatis, T. (1995). Cell 80, 529–532.

Verma, I. M., et al. (1995). Genes Dev. 9, 2723–2735.

The following experimental section and examples are offered by way of illustration and not by way of limitation.

EXAMPLES

1. Protocol for at NIK-IKK-β phosphorylation assay.

A. Reagents:

Neutralite Avidin: 20 μg/ml in PBS.

kinase: $10^{-8}$–$10^{-5}$M NIK kinase domain deletion mutant (SEQ ID NO:2, residues 2-644) at 20 μg/ml in PBS.

substrate: $10^{-7}$–$10^{-4}$M biotinylated IKK-β (SEQ ID NO:4) substrate at 40 μg/ml in PBS.

Blocking buffer: 5% BSA, 0.5% Tween 20 in PBS; 1 hour at room temperature.

Assay Buffer: 100 mM KCl, 10 mM $MgCl_2$, 1 mM $MnCl_2$, 20 mM HEPES pH 7.4, 0.25 mM EDTA, 1% glycerol, 0.5% NP-40, 50 mM BME, 1 mg/ml BSA, cocktail of protease inhibitors.

$[^{32}P]\gamma$-ATP 10×stock: $2\times10^{-5}$M cold ATP with 100 μCi $[^{32}P]\gamma$-ATP. Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

B. Preparation of assay plates:

Coat with 120 μl of stock N Avidin per well overnight at 4° C.
Wash 2 times with 200 μl PBS.
Block with 150 μl of blocking buffer.
Wash 2 times with 200 μl PBS.

C. Assay:

Add 40 μl assay buffer/well.
Add 40 μl biotinylated substrate (2–200 pmoles/40 ul in assay buffer)
Add 40 μl kinase (0.1–10 pmoles/40 ul in assay buffer)
Add 10 μl compound or extract.
Add 10 μl [$^{32}$P]γ-ATP 10×stock.
Shake at 25° C. for 15 minutes.
Incubate additional 45 minutes at 25° C.
Stop the reaction by washing 4 times with 200 μl PBS.
Add 150 μl scintillation cocktail.
Count in Topcount.

D. Controls for all assays (located on each plate):
 a. Non-specific binding
 b. cold ATP at 80% inhibition.

2. Protocol for high throughput NIKI-TRAF2 binding assay.

A. Reagents:

Neutralite Avidin: 20 μg/ml in PBS.
Blocking buffer: 5% BSA, 0.5% Tween 20 in PBS; 1 hour at room temperature.
Assay Buffer: 100 mM KCl, 20 mM HEPES pH 7.6, 1 MM MgCl$_2$, 1% glycerol, 0.5% NP-40, 50 mM β-mercaptoethanol, 1 mg/ml BSA, cocktail of protease inhibitors.
$^{33}$P NIK polypeptide 10×stock: $10^{-8}$–$10^{-6}$M "cold" NIK supplemented with 200,000–250,000 cpm of labeled NIK (Beckinan counter). Place in the 4° C. microfridge during screening.
Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (B3MB #1017128), 10 mg APMSF (BMB #917575), and 2 mM NaVO$_3$ (Sigma #S-6508) in 10 ml of PBS.
TRAF2: $10^{-7}$×$10^5$M biotinylated TRAF2 in PBS.

B. Preparation of assay plates:

Coat with 120 μl of stock N-Avidin per well overnight at 4° C.
Wash 2 times with 200 μl PBS.
Block with 150 μl of blocking buffer.
Wash 2 times with 200 μl PBS.

C. Assay:

Add 40 μl assay buffer/well.
Add 10 μl compound or extract.
Add 10 μl $^{33}$P-NIK (20–25,000 cpm/0.1–10 pmoles/well= $10^{-9}$–$10^{-7}$M final conc).
Shake at 25° C. for 15 minutes.
Incubate additional 45 minutes at 25° C.
Add 40 μM biotinylated TRAF2 (0.1–10 pmoles/40 μl in assay buffer)
Incubate 1 hour at room temperature.
Stop the reaction by washing 4 times with 200 μM PBS.
Add 150 μM scintillation cocktail.
Count in Topcount.

D. Controls for all assays (located on each plate):
 a. Non-specific binding
 b. Soluble (non-biotinylated TRAF2) at 80% inhibition.

3. Protocol for high throughput IμB-complex formation assay.

A. Reagents:

Neutralite Avidin: 20 μg/ml in PBS.
Blocking buffer: 5% BSA, 0.5% Tween 20 in PBS; 1 hour at room temperature.
Assay Buffer: 100 mM KCl, 20 mM HEPES pH 7.6, 1 mM MgCl$_2$, 1% glycerol, 0.5% NP-40, 50 mM β-mercaptoethanol, 1 mg/ml BSA, cocktail of protease inhibitors.
$^{33}$P NIK polypeptide 10×stock: $10^{-8}$–$10^{-6}$M "cold" NIK supplemented with 200,000–250,000 cpm of labeled NIK (Beckman counter). Place in the 4° C. microfridge during screening.
Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVO$_3$ (Sigma #S-6508) in 10 ml of PBS.
IκB: $10^7$–$10^5$M biotinylated IκB in PBS.
IKK-β: $10^{-7}10^5$M in PBS.

B. Preparation of assay plates:

Coat with 120 μl of stock N-Avidin per well overnight at 4° C.
Wash 2 times with 200 μl PBS.
Block with 150 μl of blocking buffer.
Wash 2 times with 200 μl PBS.

C. Assay:

Add 40 μl assay buffer/well.
Add 10 μl compound or extract.
Add 10 μl $^{33}$P-NIK (20–25,000 cpm/0.1–10 pmoles/well= $10^{-9}$–$10^{-7}$M final conc).
Shake at 25° C. for 15 minutes.
Incubate additional 45 minutes at 25° C.
Add 20 μM IKK-β(0.1–10 pmoles/20 ul in assay buffer)
Add 20 μM biotinylated IκB (0.1–10 pmoles/20 ul in assay buffer)
Incubate 1 hour at room temperature.
Stop the reaction by washing 4 times with 200 μM PBS.
Add 150 μM scintillation cocktail.
Count in Topcount.

D. Controls for all assays (located on each plate):
 a. Non-specific binding
 b. Soluble (non-biotinylated IκB) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A probe, vector or recombinant nucleic acid comprising the sequence set forth as SEQ ID NO: 1.

2. An isolated cell comprising the probe, vector or recombinant nucleic acid of claim 1.

3. A probe, vertor or recombinant nucleic acid comprising at least 24 consecutive nucleotides of SEQ ID NO: 1, which consecutive nucleotides comprise nucleotides 72–75 of the sequence set forth as SEQ ID NO:1.

4. An isolated cell comprising the probe, vector or recombinant nucleic acid of claim 3.

5. The probe, vector or recombinant nucleic acid of claim 3 comprising at least 96 consecutive nucleotides of SEQ ID NO:1, which consecutive nucleotides comprise nucleotides 72–75 of the sequence set forth as SEQ ID NO:1.

6. An isolated cell comprising the probe, vector or recombinant nucleic acid of claim 5.

7. A probe, vector or recombinant nucleic acid encoding a polypeptide comprising the amnino acid sequence set forth as SEQ ID NO:2.

8. An isolated cell conprising the probe, vector or recombinant nucleic acid of claim 7.

9. A method of making an isolated polypeptide comprising the amino acid sequence set forth as SEQ ID NO:2, said method comprising the steps of:

introducing the vector or recombinant nucleic acid of claim 7 into a host cell or cellular extract, incubating said host cell or cellular extract under conditions whereby said polypeptide is expressed; and isolating said polypeptide.

10. A probe, vector or recombinant nucleic acid encoding a polypeptide comprising at least 10 consecutive amino acid residues of the amino acid sequence set forth as SEQ ID NO:2, which consecutive amino acid residues comprise the amino acid residue 25 of SEQ ID NO:2.

11. An isolated cell comprising the probe, vector or recombinant nucleic acid of claim 10.

12. A method of making an isolated polypeptide comprising at least 10 consecutive amino acid residues of the amino acid sequence set forth as SEQ ID NO:2, which consecutive amino acid residues comprise the amino acid residue 25 of SEQ ID NO:2, said method comprising the steps of:

introducing the vector or recombinant nucleic acid of claim 10 into a host cell or cellular extract, incubating said host cell or cellular extract under conditions whereby said polypeptide is expressed; and isolating said polypeptide.

13. The probe, vector or recombinant nucleic acid according to claim 10, wherein said polypeptide has one or more activities selected from the group consisting of: kinase activity, kinase inhibitory activity, IκB kinase-α binding activity, IκB kinase-α binding inhibitory activity, IκB kinase-B binding activity, IκB kinase-β binding inhibitory activity, tumor necrosis factor receptor-associated factor 2 binding activity, tumor necrosis factor receptor-associated factor 2 binding inhibitory activity, IκB binding activity, IκB binding inhibitory activity, nuclear factor-κB activating activity and nuclear factor-κB inhibitory activity.

14. An isolated cell comprising the probe, vector or recombinant nucleic acid of claim 13.

15. A method of making an isolated polypeptide comprising at least 10 consecutive amino acid residues of the amino acid sequence set forth as SEQ ID NO:2, which consecutive amino acid residues comprise the amino acid residue 25 of SEQ ID NO:2, said method comprising the steps of:

introducing the vector or recombinant nucleic acid of claim 13 into a host cell or cellular extract, incubating said host cell or cellular extract under conditions whereby said polypeptide is expressed; and isolating said polypeptide.

* * * * *